(12) United States Patent
Belisle et al.

(10) Patent No.: US 11,731,108 B2
(45) Date of Patent: Aug. 22, 2023

(54) MIXED MODE CATION EXCHANGE CHROMATOGRAPHY LIGANDS BASED ON 1,3-DIOXOISOINDOLIN-2-YL STRUCTURES

(71) Applicant: BIO-RAD LABORATORIES, INC., Hercules, CA (US)

(72) Inventors: Christopher Belisle, Walnut Creek, CA (US); Jiali Liao, San Ramon, CA (US); Edwin Lozano, Berkeley, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 17/696,917

(22) Filed: Mar. 17, 2022

(65) Prior Publication Data

US 2022/0305460 A1    Sep. 29, 2022

Related U.S. Application Data

(60) Provisional application No. 63/162,092, filed on Mar. 17, 2021.

(51) Int. Cl.

| | |
|---|---|
| *B01J 20/28* | (2006.01) |
| *B01D 15/38* | (2006.01) |
| *B01J 20/30* | (2006.01) |
| *C07K 1/16* | (2006.01) |
| *B01J 20/285* | (2006.01) |
| *B01J 20/289* | (2006.01) |

(52) U.S. Cl.
CPC ........ *B01J 20/285* (2013.01); *B01D 15/3809* (2013.01); *B01D 15/3847* (2013.01); *B01J 20/289* (2013.01); *B01J 20/28085* (2013.01); *B01J 20/3042* (2013.01); *C07K 1/165* (2013.01); *B01J 2220/52* (2013.01)

(58) Field of Classification Search
CPC .. B01J 20/285; B01J 20/28085; B01J 20/289; B01J 20/3042; B01J 2220/52; B01D 15/3809; B01D 15/3847; C07K 1/165
See application file for complete search history.

(56) References Cited

U.S. PATENT DOCUMENTS

| | | |
|---|---|---|
| 9,309,282 B2 | 4/2016 | Liao et al. |
| 10,583,429 B2 | 3/2020 | Cramer et al. |
| 10,792,654 B2 | 10/2020 | Liao et al. |

(Continued)

FOREIGN PATENT DOCUMENTS

| | | | | |
|---|---|---|---|---|
| CN | 110240649 A | * | 9/2019 | |
| WO | WO-9609116 A1 | * | 3/1996 | ........... B01D 15/305 |

OTHER PUBLICATIONS

Machine translation of CN 110240649.*

(Continued)

*Primary Examiner* — Benjamin L Lebron
(74) *Attorney, Agent, or Firm* — Saliwanchik, Lloyd & Eisenschenk (57) ABSTRACT

The subject invention pertains to proteins are purified by a mixed-mode chromatography system formed by attaching a ligand with cation exchange and hydrophobic 1,3-dioxoisoindolin-2-yl group functionalities to a large-pore support matrix, the only linkage between the ligand and the support matrix being a chain having a backbone of one, two, three, four, or five atoms between the hydrophobic group and the support matrix.

21 Claims, 5 Drawing Sheets

(56) References Cited

U.S. PATENT DOCUMENTS

| | | |
|---|---|---|
| 2004/0020857 A1* | 2/2004 | Belew .................... B01J 41/04 |
| | | 210/683 |
| 2008/0177048 A1 | 7/2008 | Gagnon |
| 2013/0102761 A1 | 4/2013 | Liao et al. |
| 2015/0258539 A1 | 9/2015 | Cramer et al. |
| 2020/0391196 A1 | 12/2020 | Liao et al. |

OTHER PUBLICATIONS

Zhang, K. et al. "Mixed-mode chromatography in pharmaceutical and biopharmaceutical applications" *Journal of Pharmaceutical and Biomedical Analysis*, available online May 6, 2016, pp. 73-88, vol. 128.

* cited by examiner

MIXED MODE CATION EXCHANGE CHROMATOGRAPHY LIGANDS BASED ON 1,3-DIOXOISOINDOLIN-2-YL STRUCTURES

CROSS-REFERENCE TO RELATED APPLICATION

This application claims the benefit of U.S. Provisional Application No. 63/162,092, filed Mar. 17, 2021, which is hereby incorporated by reference in its entirety.

BACKGROUND OF THE INVENTION

The extraction of immunoglobulins, enzymes, recombinant proteins and other proteins from source liquids, which are primarily mammalian bodily fluids or cell culture harvests, is of value in obtaining the proteins in a sufficiently concentrated or purified form for diagnostic and therapeutic uses as well as laboratory studies in general. Purifications of proteins, and particularly immunoglobulins, often suffer however from such factors as low yield, the use of costly separation media, the leaching of separation media into the product, and concerns for the safe disposal of extraneous materials used in the extraction process. Thus, there is a need to address some of these issues.

BRIEF SUMMARY OF THE INVENTION

The present invention relates to technologies for extracting immunoglobulins, enzymes, recombinant proteins, or other proteins from source liquids for purposes of purification or isolation, with particular emphasis on chromatographic separation techniques and materials. The ligands disclosed in this application exhibit moderate hydrophobicity and a significant dipole moment (due to the dioxoisoindolin unit). The ligands also have a single pKa that is related to the carboxylic acid functionality since the amines are not protonated at operational pH. The ligand is also rigid, which enhances the hydrophobic and ion exchange properties of the ligand and the ligand is hydrolytically stable. The ligand also has two regio-isomers (5-$NH_2$ and 4-$NH_2$) and the symmetry of the ligand simplifies binding experiments.

In certain embodiments, an unusually efficient extraction (i.e. purification) of proteins, such as, for example, immunoglobulins, enzymes, recombinant proteins, and other proteins, can be achieved through the use of a mixed-mode chromatography system that combines cationic exchange (CEX) and hydrophobic functionalities with a large-pore support matrix. In certain embodiments, the protein to be purified is an antibody. The cationic exchange and hydrophobic functionalities can be incorporated in a ligand that is bound to a solid matrix that has pores whose median diameter is 0.5 micron or greater, and having substantially no pores of less than 0.1 micron in diameter, and the ligand is coupled to the support matrix via the hydrophobic group on the ligand through a linkage of a chain of one, two, three, four, or five atom(s). Binding of proteins to the matrix-supported ligand can be achieved at low pH, and elution of the bound proteins is achieved at a higher pH, using conventional binding and elution conditions. Highly purified immunoglobulin in high yield, for example, is achieved with a single pass of the source liquid through the separation medium. The separation medium, i.e., the matrix-supported ligand, is itself novel, as is the method of attachment of the ligand to the matrix.

In some embodiments, a method for purifying a protein, such as, for example, an antibody, from a source solution comprises contacting the source solution with a mixed-mode chromatography medium comprising a ligand coupled to a solid support. In certain embodiments, the ligand can have a hydrophobic group and carboxyl group. In certain embodiments, the solid support can have pores of a median diameter of 0.5 micron or greater with substantially no pores of 0.1 micron or less in diameter. In certain embodiments, the ligand can be coupled to the solid support via the hydrophobic group through a chain of one, two, three, four, or five atom(s), to bind the protein, such as, for example, the antibody, in the source solution to the solid support through the ligand. In certain embodiments, the bound protein (e.g., antibody) can be eluted from the solid support. In some embodiments, the contacting step is performed at a pH of about 4.0 to about 6.0, about 4.25 to about 4.75, or about 4.5 and the eluting step is performed at a pH of from about 6.1 to about 8.5, about 7.25 to about 7.75, or about 7.5. In some embodiments, the solid support comprises particles having a median particle size of from about 25 microns to about 150 microns. In some embodiments, the solid support is a membrane or a monolith.

In some embodiments, a mixed-mode chromatography medium is provided. In some embodiments, the mixed-mode medium comprises a ligand coupled to a solid support, the ligand comprising a hydrophobic group and a carboxyl group. In certain embodiments, the solid support can have particles with pores of a median diameter of 0.5 micron or greater with substantially no pores of 0.1 micron or less in diameter. In certain embodiments, the ligand can be coupled to the solid support at the hydrophobic group by a chain of one, two, three, four, or five atoms.

Also provided herein is a method for manufacturing a mixed-mode chromatography medium, comprising oxidizing diol groups on diol-functionalized solid particles that can have pores of a median diameter of 0.5 micron or greater with substantially no pores of 0.1 micron or less in diameter. The diol density can be from about 200 to about 300 μmol/mL to aldehyde groups, thereby converting the diol-functionalized solid particles to aldehyde-functionalized solid particles. In certain embodiments, functionalized ligands can be coupled to the aldehyde-functionalized particles. The functionalized ligands can have a hydrophobic group joined to a carboxyl group.

In some embodiments of the methods, mediums, and/or systems, the hydrophobic group of the ligand is a 1,3 dioxoisoindolin-2-yl group. In certain embodiments, the carboxyl group of the ligand is a carboxylic acid, such as, for example, acetic acid (ethanoic acid), propanoic acid, butanoic acid, pentanoic acid, or hexanoic acid. In some embodiments, the ligand is 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, and/or 4-(4-amino-1,3-dioxoisoindolin-2-yl)butanoic acid.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. In the context of pH measurements, the terms "about" or "approximately" permit a variation of ±0.1 unit from a stated value.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

As used herein, the term "chain" is used to denote a series of atoms joined together in a linear arrangement, preferably by single bonds, such as -A-B-C-... etc. in which the atoms are either all the same bond or contain one or more bond that differ from the other(s) (e.g., double bonds or triple bonds). The term includes both substituted and unsubstituted chains.

As used herein, the term "substituted" refers to atoms or groups other than hydrogen atoms, such as for example —OH, —NH$_2$, and =O, but in all cases, the number of atoms indicated as constituting the chain, such as in the expression "chain of one to three atoms," refers to the atoms in the linear array, excluding any hydrogen atoms and any substituent groups. The linearly arranged atoms are also referred to as the backbone of the chain.

As used herein, the term "monolith" is meant to indicate a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores. When in the form of spheres or beads, the median particle diameter, in which the term "diameter" refers to the longest exterior dimension of the particle, is preferably within the range of about 25 microns to about 150 microns.

As used herein, the term "antibody" refers to an immunoglobulin, composite (e.g., fusion), or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. The term may also include composite forms such, for example, fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

As used herein, "bind-elute mode" refers to an operational approach to chromatography in which the buffer conditions are established so that target molecules and, optionally undesired contaminants, bind to the ligand when the sample is applied to the ligand. Fractionation of the target can be achieved subsequently by changing the conditions such that the target is eluted from the support. In some embodiments, contaminants remain bound following target elution. In some embodiments, contaminants either flow-through or are bound and eluted before elution of the target.

Structural groups that are useful as hydrophobic functionalities in the ligands described herein include 1,3-dioxoisoindolin-2-yl groups. Structural groups that are useful as cationic exchange (CEX) functionalities include carboxylic acids. In certain embodiments, the carboxylic acid can be, for example, formic acid, acetic acid, propionic acid, butanoic acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, or arachidic acid. The cationic exchange and hydrophobic moieties are joined at the nitrogen atom of the 1,3-dioxoisoindolin-2-yl group.

In certain embodiments, a linkage can join the ligand to the support matrix (also referred to herein as a solid support) is a chain whose one end is directly coupled to the hydrophobic functionality of the ligand and whose other end is directly coupled to the matrix, the chain thereby including any group pendant from the matrix as a result of activation of the matrix for the coupling reaction. No spacer in addition to this linkage is included. The chain can comprise one, two, three, four, or five atoms, preferably one to three atoms. Examples of such a chain are those having the formula $R^1$—$R^2$—$R^3$—, $R^1$—$R^2$—$R^3$—$R^4$—, $R^1$—$R^2$—$R^3$—NH—$R^4$— or —$R^3$—NH—$R^4$— in which $R^1$, $R^2$, $R^3$, and $R^4$ are methyl or ethyl groups and any one of $R^1$, $R^2$, $R^3$, and $R^4$ or any combination thereof can be absent. A specific example of such a group is —$CH_2$—$CH_2$—$CH_2$—C— or —$CH_2$—NH—. In some embodiments, the ligand is 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, and/or 4-(4-amino-1,3-dioxoisoindolin-2-yl)butanoic acid. In certain embodiments, a particularly convenient linkage between the 1,3-dioxoisoindolin-2-yl group of the ligand and the matrix is one in which the amine group of the ligand is bonded to the chain.

An example of a compound that can form both the ligand and, optionally, at least part of the linkage is 2-(5-amino-1,3-dioxoisoindolin-2-yl)acetic acid; the formula is as follows:

Chemical Formula: $C_{10}H_8N_2O_4$
Molecular Weight: 220.18

Another example of a compound that can form both the ligand and, optionally, at least part of the linkage is 4-(5-amino-1,3-dioxoisoindolin-2-yl)butanoic acid; the formula is as follows:

Chemical Formula: $C_{12}H_{12}N_2O_4$
Molecular Weight: 248.24

Another example of a compound that can form both the ligand and, optionally, at least part of the linkage is 2-(4-amino-1,3-dioxoisoindolin-2-yl)acetic acid; the formula is as follows:

Chemical Formula: $C_{10}H_8N_2O_4$
Molecular Weight: 220.18

Another example of a compound that can form both the ligand and, optionally, at least part of the linkage is 4-(4-amino-1,3-dioxoisoindolin-2-yl)butanoic acid; the formula is as follows:

Chemical Formula: $C_{12}H_{12}N_2O_4$
Molecular Weight: 248.24

The support matrix, as noted above, is one with pores of a median diameter of 0.5 micron or greater, with substantially no pores of less than 0.1 micron in diameter. In certain embodiments of the invention, the median pore diameter ranges from about 0.5 micron to about 2.0 microns. The pore volume can vary, although in many embodiments, the pore volume will range from about 0.5 to about 2.0 cm$^3$/g (mL/g). The matrix can be particles, a membrane, or a monolith. Disclosures of matrices meeting the descriptions in this paragraph and the processes by which they are made are found in Hjertén et al., U.S. Pat. No. 5,645,717; Liao et al., U.S. Pat. No. 5,647,979; Liao et al., U.S. Pat. No. 5,935,429; and Liao et al., U.S. Pat. No. 6,423,666. Examples of monomers that can be polymerized to achieve useful matrices are vinyl acetate, vinyl propylamine, acrylic acid, methacrylate, butyl acrylate, acrylamide, methacrylamide, and/or vinyl pyrrolidone (vinyl pyrrolidinone); the monomers can optionally have functional groups. Crosslinking agents are also of use in many embodiments and, when present, will generally constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide.

For purposes of the formation of a linkage with the ligand, and particularly ligands with amine groups, the inclusion of monomers with vicinal diols is often useful. One example is allyloxy propandiol (3-allyloxy-1,2-propanediol). Vicinal diol monomers can be used with other monomers to prepare copolymers. The diol group density in the polymers produced from diol-containing monomers can vary widely, such as for example densities within a range of from about 100 to 1,000 µmol/mL (i.e., micromoles of diol per milliliter of packed beads), and in many cases a range of from about 200 to 300 µmol/mL. An example of a matrix that meets this description and is commercially available is UNOsphere™ Diol (Bio-Rad Laboratories, Inc., Hercules, Calif., USA). To couple a pendant amine-containing ligand to a matrix with exposed vicinal diols, the diols can be oxidized to aldehyde groups, and the aldehyde groups can then be coupled to amine groups to form secondary amino linkages, all by conventional chemistry techniques well known in the art.

Protein purification utilizing a resin (i.e., separation medium) in accordance with the present invention can be achieved by conventional means known to those of skill in the art. Examples of proteins include but are not limited to antibodies, enzymes, growth regulators, clotting factors, transcription factors, and phosphoproteins. In many such conventional procedures, the resin prior to use is equilibrated with a buffer at the pH that will be used for the binding of the target protein (e.g., antibody or non-antibody protein). Equilibration can be done with respect to all features that will affect the binding environment, including ionic strength and conductivity when appropriate.

In some embodiments, the resins described herein can be used in "bind-elute" mode to purify a target protein from a biological sample. In some embodiments, following binding of the target protein to the resin, a change in pH can be used to elute the target protein.

In some embodiments, once the resin is equilibrated, the source liquid is loaded onto the resin while maintaining the source liquid, and any additional carrier liquid when used, at a pH below 6.0 with an appropriate buffer, allowing the target protein to bind to the resin. Notably, it has been found that the mixed mode resins described herein function with solutions having salt concentrations in the range of salt concentrations of cell cultures of about 50 mM to about 300 mM, about 100 mM to about 300 mM, or about 100 mM to about 150 mM. Thus, in some embodiments, the protein is loaded to the resin under such salt concentrations. Non-limiting examples of buffers suitable for use in connection with the disclosed chromatography resin include acetate buffers (e.g., sodium acetate), acetic acid, malonic acid, phosphate buffers (e.g., monosodium, disodium, and/or trisodium phosphate buffers), potassium phosphate (monobasic and/or dibasic) buffers, HEPES (2-[4-(2-hydroxyethyl)piperazin-1-yl]ethanesulfonic acid), BICINE (N,N-Bis(2-hydroxyethyl)glycine), TRIS (Tris(hydroxymethyl)aminomethane), MES (2-Morpholinoethanesulfonic acid monohydrate or ACES (N-(2-Acetamido)-2-aminoethanesulfonic acid) buffers. The buffers are, generally, prepared at concentrations of about 10 mM to about 100 mM, or about 20-50 mM.

In some embodiments, the resin is then washed with a wash liquid (buffer), optionally at the same pH as that of the loading step, to remove any unbound proteins or substances that may have been present in the source liquid. The bound protein (e.g., antibody or non-antibody protein, as desired) can be subsequently eluted with an elution buffer. Isocratic elution, stepwise elution in which buffer conditions or salt conditions are changed, or gradient elution using, for example, a buffer at a constant pH and a salt gradient (see, for example, Example 2) can be used for eluting a protein of interest.

In some embodiments, the protein is then eluted with an elution liquid (buffer) at a pH of at least 6.0. Illustrative pH ranges, as cited above, are pH of about 4.0 to about 6.0, about 4.25 to about 4.75, or about 4.5 for the, equilibration, binding (loading) and washing steps, and a pH of about 6.1 to about 8.5, about 7.25 to about 7.75, or about 7.5 for the elution step. If stepwise elution is utilized, then buffers having the same buffering agent but different pH values can be used to elute protein.

In other embodiments, the binding and washing steps are performed with the inclusion of at least one salt in the sample and wash liquids. Examples of salts that can be used for this purpose are alkali metal and alkaline earth metal halides, notably sodium and potassium halides, and as a specific example sodium chloride. The concentration of the salt can vary; in most cases, an appropriate concentration will be one within the range of about 10 mM to about 1 M, about 20 mM to about 150 mM, about 20 mM, or about 150 mM. Optimal elution conditions for some proteins can involve a buffer with a higher salt concentration than that of the binding buffer, and in other cases by a buffer with a lower salt concentration than that of the binding buffer. In some instances, bound proteins can be eluted with a salt gradient (see, for example, Example 2, below). In other embodiments, a stepwise elution can be utilized in which the amount of salt contained within a buffer is altered (e.g., increased) and passed over the column to elute bound protein.

The resin can be utilized in any conventional configuration, including packed columns and fluidized or expanded-bed columns, and by any conventional method, including batchwise modes for loading, washes, and elution, as well as continuous or flow-through modes. The use of a packed flow-through column is particularly convenient, both for preparative-scale extractions and analytical-scale extractions. A column may thus range in diameter from about 1 mm to 1 about m, and in height from about 1 cm to about 30 cm or more.

Any antibody preparation can be used in the present invention, including unpurified or partially purified antibodies from natural, synthetic, and/or recombinant sources. Unpurified antibody preparations can come from various sources such as, for example, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination thereof. In some embodiments, the antibodies have not been purified by protein A affinity prior to purification.

In certain embodiments, the resins can be used for purification of non-antibody proteins, including therapeutic proteins. Examples of therapeutic proteins include, but are not limited to, Factor VIII von Willebrand Factor enzymes, growth regulators, clotting factors, transcription factors and phosphoproteins.

In certain embodiments, a number of advantages are conferred by the methods, systems, and mixed-mode chromatographic mediums provided in the subject invention, particularly conferred by the 1,3-dioxoisoindolin-2-yl group of the ligand when compared to the existing ligand (4-aminobenzamidoacetic acid) used in the cPrime resin (Bio-Rad®, Hercules, Calif.). The ligands of the subject invention provide a moderate hydrophobic nature coupled with greater dipole moment interaction of dioxoisoindolin unit. The ligands provide a single pKa from COOH— amines are not protonated at operational pH. The ligands are rigid, which enhances the hydrophobic and IEX properties of ligand. The "double" amide of the ligand is hydrolytically stable, which provides a greater pH stability. There are two regio-isomers (5-$NH_2$/4-$NH_2$) of the ligand, specifically in the hydrophobic group, provided by the subject invention; this ligand symmetry simplifies binding experiments.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Preparation of Functionalized Resin

UNOsphere™ Diol (10 mL), a copolymer of 3-allyloxy-1,2-propanediol and vinyl pyrrolidinone, crosslinked with N,N'-methylenebisacrylamide and with a diol density of 200-300 μmol/mL, was used in the form of spherical beads. The beads were suspended in 10 mL of either 0.1 M sodium acetate or water. Sodium periodate was added to a concentration within the range of 50 to 100 mM, and the resulting mixture was incubated at room temperature (approximately 21° C.) for about 3 to about 24 hours. The reaction resulted in conversion of the diol groups to aldehyde groups in the range of 150-250 μmol/mL. The resulting aldehyde-functionalized resin was transferred to a 20-mL column where it was washed with 100 mL of water.

The washed resin was then suspended in 10 mL of water and mixed with 2-(5-amino-1,3-dioxoisoindolin-2-yl)acetic acid in 3 mL of tetrahydrofuran (THF), and the resulting mixture was incubated in a shaker at 200 rpm for thirty minutes at 37° C. To the mixture was then added NaBH₃CN (100 mg), and the concentration of 2-(5-amino-1,3-dioxoisoindolin-2-yl)acetic acid in the reaction mixture was in the range of 25 mM to 100 mM. After three hours of reaction time, the resulting 2-(5-amino-1,3-dioxoisoindolin-2-yl)acetic acid-functionalized resin was transferred to a 20-mL column where it was washed with three column volumes of water followed by one to two column volumes of 0.1N aqueous NaOH, then washed with water again until the pH of the eluent was below 10. The 2-(5-amino-1,3-dioxoisoindolin-2-yl)acetic acid ligand density in the resulting product was in the range of 25-100 μmol/mL. The preparation of the 2-(5-amino-1,3-dioxoisoindolin-2-yl)acetic acid-functionalized resin is as follows with the grey orb representing UNOsphere™ Diol spherical beads:

The same method of functionalization is repeated for ligands 4-(5-amino-1,3-dioxoisoindolin-2-yl)butanoic acid, 2-(4-amino-1,3-dioxoisoindolin-2-yl)acetic acid, and 4-(4-amino-1,3-dioxoisoindolin-2-yl)butanoic acid.

Example 2

Myo, Rib A, and Cyt C Binding to Functionalized Resin

A column measuring 7 mm in inner diameter and 5.5 cm in length was packed with the 2-(5-amino-1,3-dioxoisoindolin-2-yl)acetic acid-functionalized resin, 4-(5-amino-1,3-dioxoisoindolin-2-yl)butanoic acid-functionalized resin, 2-(4-amino-1,3-dioxoisoindolin-2-yl)acetic acid-functionalized resin, or 4-(4-amino-1,3-dioxoisoindolin-2-yl)butanoic acid-functionalized resin prepared in Example 1 and equilibrated with 20 mM sodium phosphate pH 7.0. A 250 ul of solution of proteins in this buffer was then applied to the column at a flow rate of 2 mL/min. The proteins in the solution were myoglobin (Myo), ribonuclease A (Rib A), and cytochrome C (Cyt C). Proteins were eluted with 20 ml linear gradient elution from 20 mM sodium phosphate pH 7.0 to 20 mM sodium phosphate pH 7.0 containing 500 mM NaCl (see Table 1).

TABLE 1

| Sample | Ligand lot | Reaction conditions | Ligand mmol eq. | Ion Exchange capacity (IC)(ueq/ml) | Retention time of Myo | Retention time of Rib A | Retention time of Cyt C |
|---|---|---|---|---|---|---|---|
| cPrime | | | | 129 | 2.24 | 8.09 | 10.37 |
| 6622-73 | 2-(5-amino-1,3-dioxoisoindolin-2-yl)acetic acid (CB419j) | 30% (THF) at 37° C. | 2 | 107 | 2.28 | 8.06 | 10.26 |
| 6657-20-1 | CB419j | 30% THF + RT | 2 | 80 | 2.35 | 8.15 | 9.87 |
| 6622-74-1 | 4-(5-amino-1,3-dioxoisoindolin-2-yl)butanoic acid (CB422) | 30% THF + 37° C. | 2 | 72 | 2.27 | 6.99 | 9.06 |
| 6622-74-2 | 2-(4-amino-1,3-dioxoisoindolin-2-yl)acetic acid (CB424) | 30% THF + 37° C. | 2 | 69 | 2.31 | 8.38 | 9.34 |
| 6622-74-3 | 4-(4-amino-1,3-dioxoisoindolin-2-yl)butanoic acid (CB425) | 30% THF + 37° C. | 2 | 54 | 2.24 | 6.58 | 7.89 |

Figure 1A:
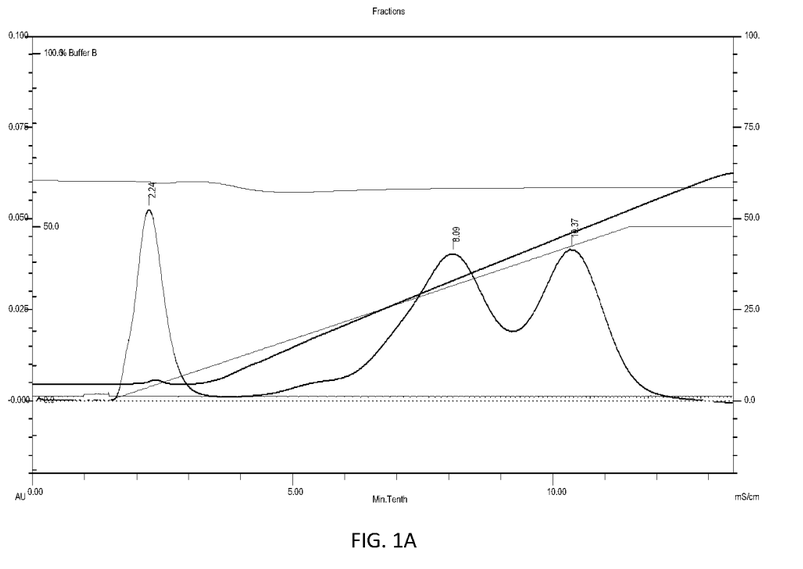
FIGS. 1A-1B show chromatographs of proteins mixture separation using ligands p-aminohuppuric acid (Nuvia cPrime) (FIG. 1A) and 2-(5-amino-1,3-dioxoisoindolin-2-yl)acetic acid (CB419) (FIG. 1B) functionalized in resins in which myoglobin (Myo), ribonuclease A (Rib A), and cytochrome C (Cyt C) proteins are separated by passing the samples through columns with the aforementioned functionalized ligands. The elution peak of Myo is at a retention time of about 2.24 to about 2.28. The elution peak of Rib A is at a retention time of about 8.06 to about 8.09. The elution peak of Cyt C is at a retention time of about 10.26 to about 10.37.
Figure 1B:
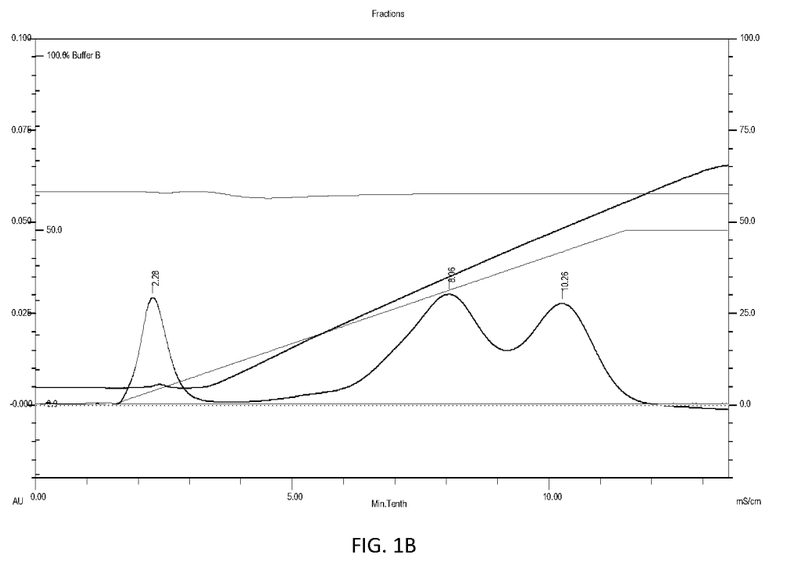

Myo, Rib A, and Cyt C were separated and identified using ligands 4-aminobenzamidoacetic acid (FIG. 1A) and 2-(5-amino-1,3-dioxoisoindolin-2-yl)acetic acid (CB419) (FIG. 1B) in the functionalized in resins. The elution peak of Myo is at a retention time of about 2.24 to about 2.28. The elution peak of Rib A is at a retention time of about 8.06 to about 8.09. The elution peak of Cyt C is at a retention time of about 10.26 to about 10.37. Both the 4-aminobenzamidoacetic acid-functionalized resin and 2-(5-amino-1,3-dioxoisoindolin-2-yl)acetic acid-functionalized resin have similar protein separation retention time and efficiency.

Figure 2A:
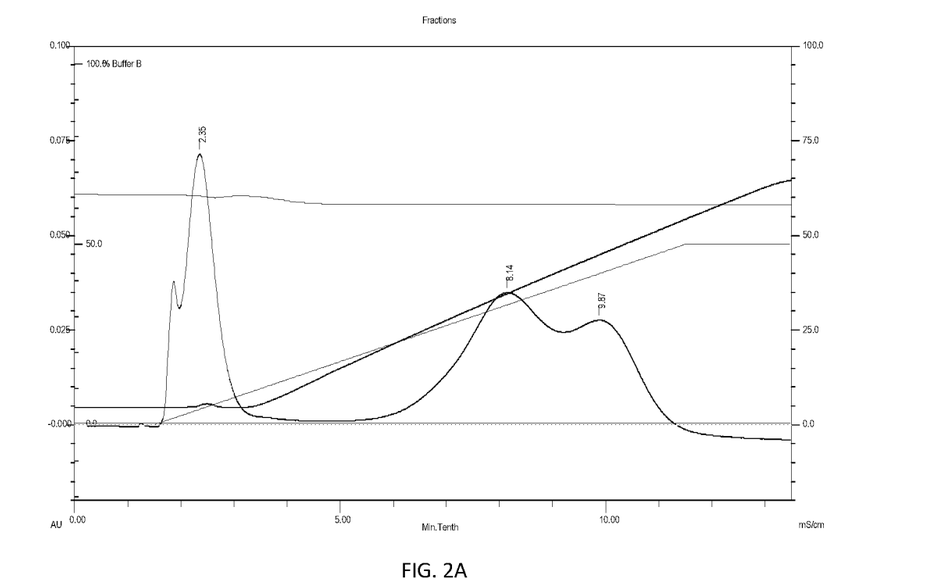
FIGS. 2A-2B show chromatographs of proteins mixture separation using ligand 2-(5-amino-1,3-dioxoisoindolin-2-yl)acetic acid (CB419) having an ion exchange capacity (IC) of 80 ueq/ml (FIG. 2A) and 107 ueq/ml (FIG. 2B) in the functionalized resins in which Myo, Rib A, and Cyt C proteins are separated by passing the samples through columns with the aforementioned functionalized ligands. The elution peak of Myo is at a retention time of about 2.28 to about 2.35. The elution peak of Rib A is at a retention time of about 8.06 to about 8.15. The elution peak of Cyt C is at a retention time of about 9.87 to about 10.26.
Figure 2B:
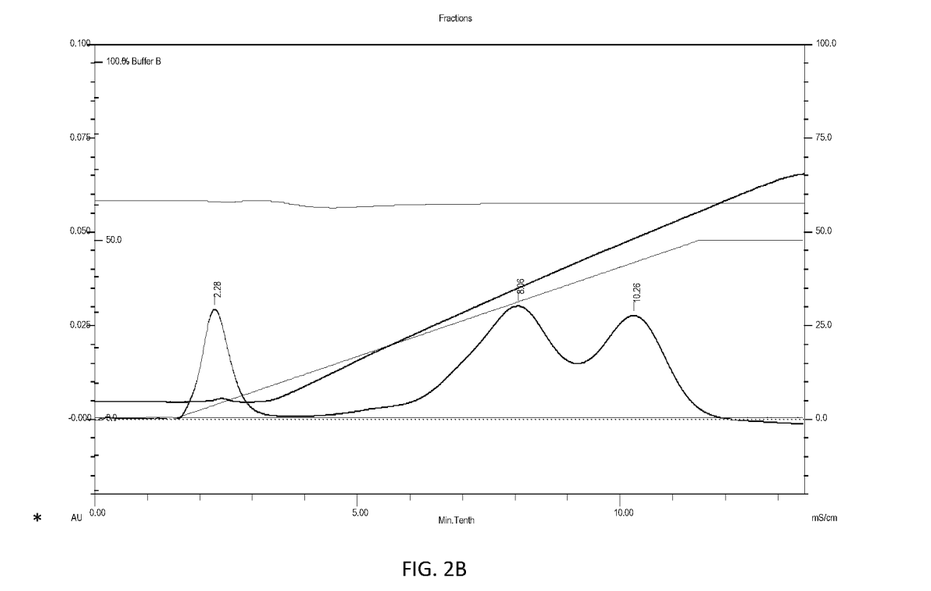

Proteins were also separated and identified using ligand 2-(5-amino-1,3-dioxoisoindolin-2-yl)acetic acid (CB419) having an IC of 80 ueq/ml (FIG. 2A) and at 107 ueq/ml (FIG. 2B) in the functionalized resins Myo, Rib A, and Cyt C were passed through columns with the aforementioned functionalized ligands followed by HPLC. The elution peak of Myo is at a retention time of about 2.28 to about 2.35. The elution peak of Rib A is at a retention time of about 8.06 to about 8.15. The elution peak of Cyt C is at a retention time of about 9.87 to about 10.26. Results show that resins with different ligand concentrations have similar protein retention.

Figure 3A:
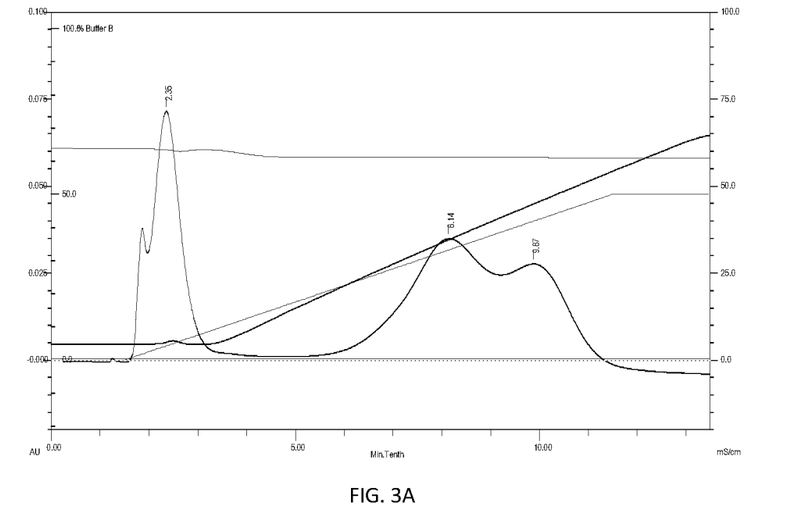
FIGS. 3A-3B show chromatographs of proteins mixture separation using ligands 2-(5-amino-1,3-dioxoisoindolin-2-yl)acetic acid (CB419) having an IC of 80 ueq/ml (FIG. 3A) and 4-(5-amino-1,3-dioxoisoindolin-2-yl)butanoic acid (CB422) having an IC of 72 ueq/ml (FIG. 3B) in the functionalized resins in which Myo, Rib A, and Cyt C proteins are separated by passing the samples through columns with the aforementioned functionalized ligands. The elution peak of Myo is at a retention time of about 2.27 to about 2.35. The elution peak of Rib A is at a retention time of about 6.99 to about 8.15. The elution peak of Cyt C is at a retention time of about 9.06 to about 9.87.
Figure 3B:
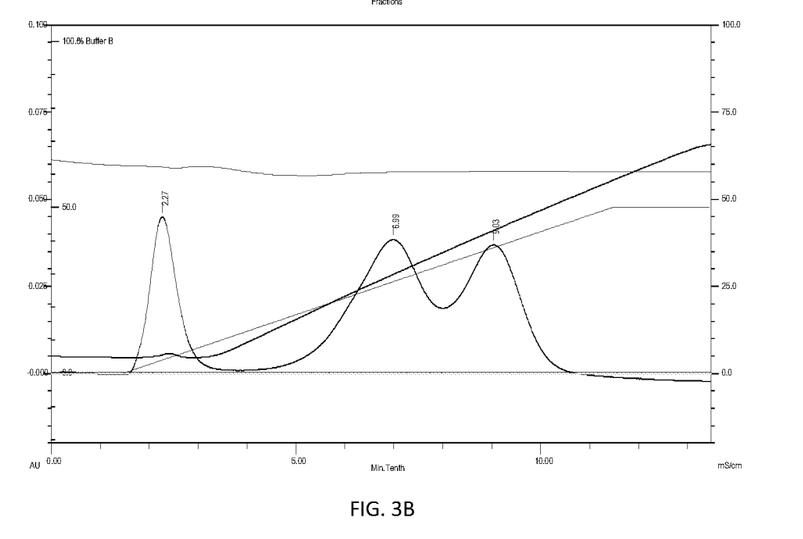

Proteins were separated and identified using ligands 2-(5-amino-1,3-dioxoisoindolin-2-yl)acetic acid (CB419) having an IC of 80 ueq/ml (FIG. 3A) and 4-(5-amino-1,3-dioxoisoindolin-2-yl)butanoic acid (CB422) at a IC of 72 ueq/ml (FIG. 3B) in functionalized resins. Myo, Rib A, and Cyt C are passed through columns with the aforementioned functionalized ligands followed by HPLC. The elution peak of Myo is at a retention time of about 2.27 to about 2.35. The elution peak of Rib A is at a retention time of about 6.99 to about 8.15. The elution peak of Cyt C is at a retention time of about 9.06 to about 9.87. Results show that resins with different ligands CB419 and CB422 have similar separation efficiencies of Rib A and Cyt C. CB422 has slightly lower hydrophobicity than CB419.

Figure 4A:
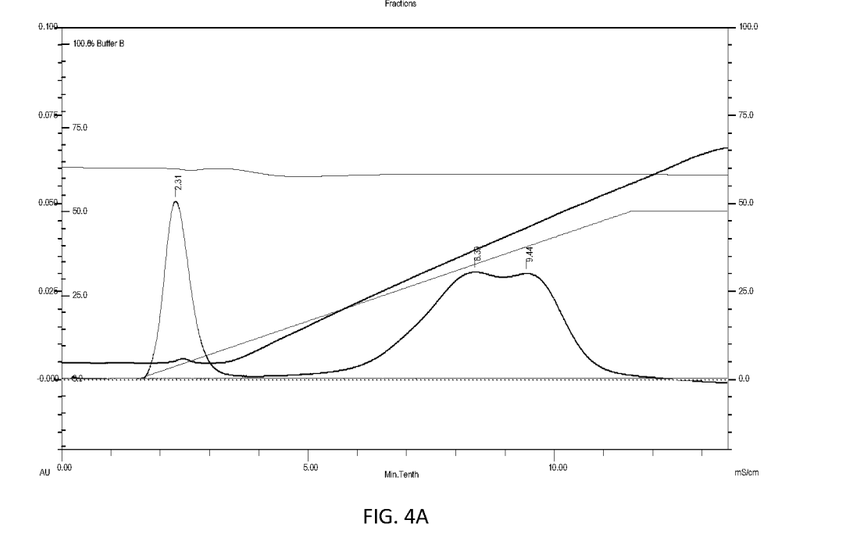
FIGS. 4A-4B show chromatographs of proteins mixture separation using ligands 2-(4-amino-1,3-dioxoisoindolin-2-yl)acetic acid (CB424) having an IC of 69 ueq/ml (FIG. 4A) and 4-(4-amino-1,3-dioxoisoindolin-2-yl)butanoic acid (CB425) having an IC of 54 ueq/ml (FIG. 4B) in the functionalized resins in which Myo, Rib A, and Cyt C proteins are separated by passing the samples through columns with the aforementioned functionalized ligands followed. The elution peak of Myo is at a retention time of about 2.24 to about 2.31. The elution peak of Rib A is at a retention time of about 6.58 to about 8.38. The elution peak of Cyt C is at a retention time of about 7.89 to about 9.44.
Figure 4B:
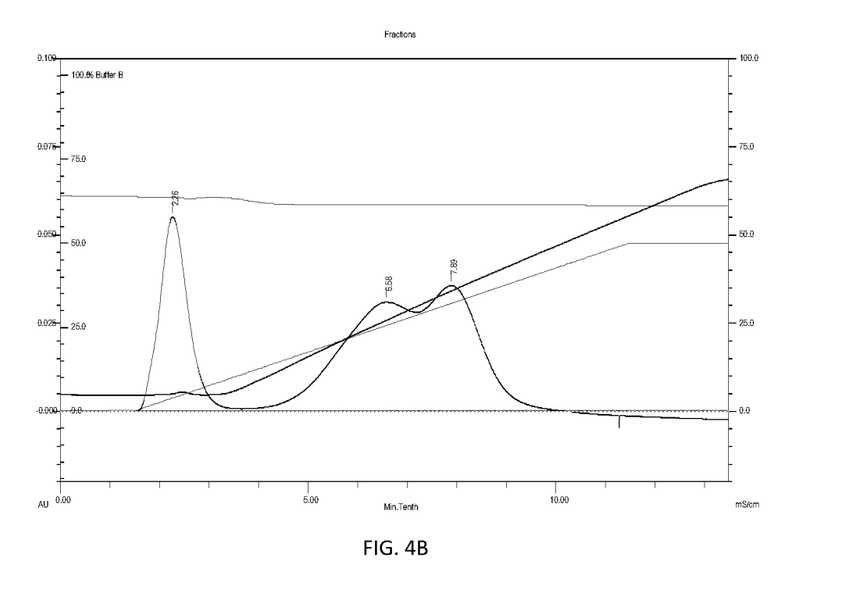
Figure 5:
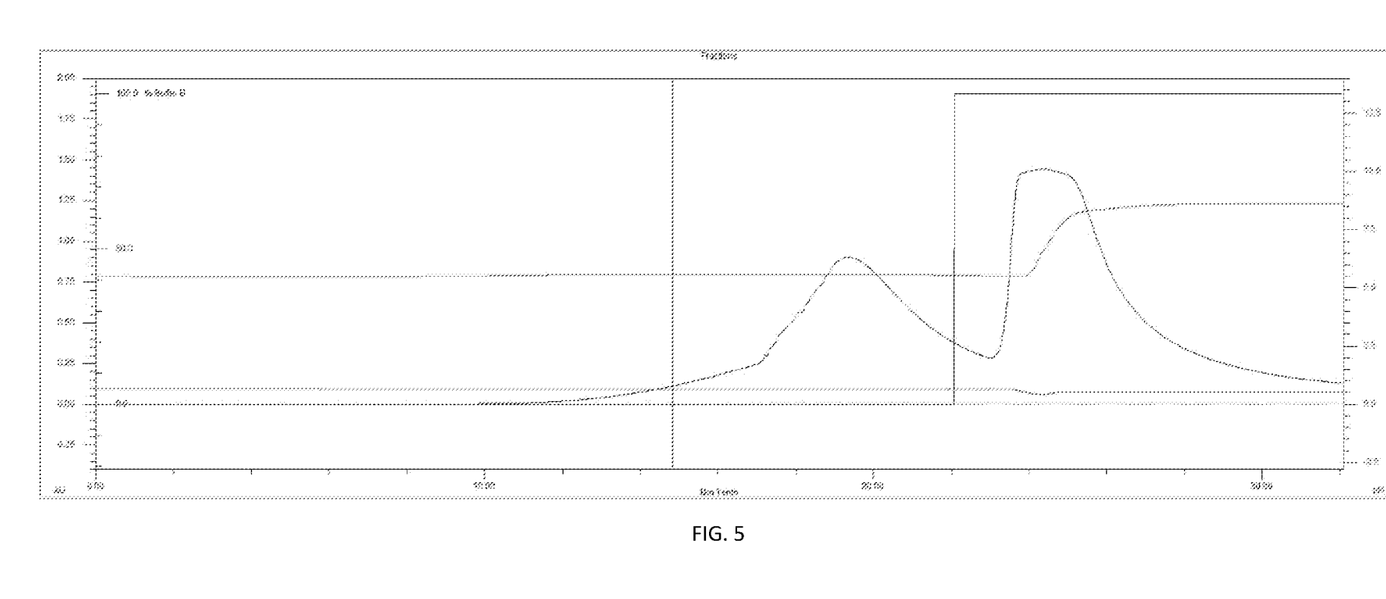
FIG. 5 shows a chromatograph of IgG binding capacity measurement using ligand 4-(4-amino-1,3-dioxoisoindolin-2-yl)butanoic acid (CB425) having an IC of 54 ueq/ml in the functionalized resins in which human IgG is passing the samples through columns with the aforementioned functionalized ligand.

Protein were also separated and identified using ligands 2-(4-amino-1,3-dioxoisoindolin-2-yl)acetic acid (CB424) having an IC of 69 ueq/ml (FIG. 4A) and 4-(4-amino-1,3-dioxoisoindolin-2-yl)butanoic acid (CB425) having an IC of 54 ueq/ml (FIG. 4B) in the functionalized resins. Myo, Rib A, and Cyt C were passed through columns with the aforementioned functionalized ligands followed by HPLC. The elution peak of Myo is at a retention time of about 2.24 to about 2.31. The elution peak of Rib A is at a retention time of about 6.58 to about 8.38. The elution peak of Cyt C is at a retention time of about 7.89 to about 9.44. Results show that resins with ligands 2-(4-amino-1,3-dioxoisoindolin-2-yl)acetic acid (CB424) or 4-(4-amino-1,3-dioxoisoindolin-2-yl)butanoic acid (CB425), compared with CB419 and CB422, have similar hydrophobicity, but they both have low separation efficiency for Rib A and Cyt C.

Example 3

IgG Binding to Functionalized Resin

Individual columns measuring 7 mm in inner diameter and 5.5 cm in length were packed with the 2-(5-amino-1,3-dioxoisoindolin-2-yl)acetic acid (CB419), 4-(5-amino-1,3-dioxoisoindolin-2-yl)butanoic acid (CB422) 2-(4-amino-1,3-dioxoisoindolin-2-yl)acetic acid (CB424), and 4-(4-amino-1,3-dioxoisoindolin-2-yl)butanoic acid (CB425) prepared in Example 1 and equilibrated with 20 mM sodium acetate buffer containing 150 mM NaCl at pH 4.5. A 4.14 mg/mL solution of IgG in this buffer was then applied to the column at a flow rate of 1 mL/min until uv absorption reach 10% breakthrough. The column was than wash with 10 ml equilibration buffer followed by 20 ml of isocratic elution buffer of 100 mM sodium phosphate pH 7.5. The collected protein in the elution fractions of each column was analyzed by UV to determine the protein recovery (See Table 2).

TABLE 2

| Sample | Prototype | Binding Capacity (mg/mL) | % Recovery |
|---|---|---|---|
| 6622-73-1 | CB419 | 41 | 93% |
| 6622-74-1 | CB422 | 40 | 92% |
| 6622-74-2 | CB424 | 40 | 79% |
| 6622-74-3 | CB425 | 32 | 85% |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A mixed-mode chromatography medium comprising one or more ligand coupled to a solid support, said ligand comprising a 1,3-dioxoisoindolin-2-yl group, said solid support having pores of a median diameter of 0.5 micron or greater with substantially no pores of 0.1 micron or less in diameter, and said ligand coupled to said solid support at a 1,3-dioxoisoindolin-2-yl group through a chain of one to five atoms.

2. The mixed-mode chromatography medium of claim 1, wherein the solid support comprises particles and said particles have a median particle size of from about 25 microns to about 150 microns.

3. The mixed-mode chromatography medium of claim 1, wherein the ligand is 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, and/or 4-(4-amino-1,3-dioxoisoindolin-2-yl)butanoic acid.

4. The mixed-mode chromatography medium of claim 1, wherein the mixed-mode chromatography medium has a dynamic binding capacity of at least about 30 mg of IgG per mL of mixed-mode chromatography medium.

5. A composition comprising the mixed-mode chromatography medium of claim 1 and a source solution or a buffer.

6. The composition of claim 5, wherein the source solution comprises non-antibody target proteins, monomeric antibodies and/or antibody aggregates.

7. The composition of claim 5, wherein said source solution or buffer contains a salt selected from alkali metal and alkaline earth metal halides at a concentration of from about 50 mM to about 300 mM.

8. The composition of claim 5, wherein said source solution or buffer contains a salt selected from alkali metal and alkaline earth metal halides at a concentration of from about 100 mM to about 150 mM.

9. A method for manufacturing a mixed-mode chromatography medium, said method comprising:
   i) oxidizing diol groups on diol-functionalized solid particles having pores of a median diameter of 0.5 micron or greater with substantially no pores of 0.1 micron or less in diameter and having a diol density of from about 200 to about 300 μmol/mL to aldehyde groups, thereby converting said diol-functionalized solid particles to aldehyde-functionalized solid particles; and
   ii) coupling functionalized ligands to said aldehyde-functionalized solid particles, said functionalized ligands comprising a 1,3-dioxoisoindolin-2-yl hydrophobic group joined to a carboxyl group.

10. The method of claim 9, wherein the ligands are 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, and/or 4-(4-amino-1,3-dioxoisoindolin-2-yl)butanoic acid.

11. The method of claim 9, wherein the functionalized ligands comprising the 1,3-dioxoisoindolin-2-yl hydrophobic group joined to the carboxyl group, and wherein:
   the ligand and carboxyl group together constitute 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, or 4-(4-amino-1,3-dioxoisoindolin-2-yl)butanoic acid,
   the solid support is a copolymer of 3-allyloxy-1,2-propanediol and vinyl pyrrolidinone crosslinked with N,N'-methylenebisacrylamide, and
   the solid support is coupled directly to an amine group on the 1,3-dioxoisoindolin-2-yl hydrophobic group.

12. The method of claim 9, wherein the mixed-mode chromatography medium has a dynamic binding capacity of at least about 30 mg of IgG per mL of mixed-mode chromatography medium.

13. A method for purifying a protein from a source solution, said method comprising:
   i) contacting said source solution with a mixed-mode chromatography medium comprising a ligand coupled to a solid support, said ligand comprising a 1,3-dioxoisoindolin-2-yl hydrophobic group and a carboxyl group, wherein said hydrophobic group is joined to said acid moiety, said solid support having pores of a median diameter of 0.5 micron or greater with substantially no pores of 0.1 micron or less in diameter, and said ligand coupled to said solid support at said hydrophobic group through a chain of one to five atoms, to bind said protein in said source solution to said solid support through said ligand; and
   ii) eluting said protein so bound from said solid support.

14. The method of claim 13, wherein said protein is an antibody.

15. The method of claim 13, wherein step (a) is performed at a pH of about 4.0 to about 6.0 and step (b) is performed at a pH of from about 6.1 to about 8.5.

16. The method of claim 13, wherein said ligand is 2-(5-amino-1,3-dioxoisoindolin-2-yl)acetic acid, 4-(5-amino-1,3-dioxoisoindolin-2-yl)butanoic acid, 2-(4-amino-1,3-dioxoisoindolin-2-yl)acetic acid, and/or 4-(4-amino-1,3-dioxoisoindolin-2-yl)butanoic acid.

17. The method of claim 13, wherein said solid support consists of particles having a median particle size of from about 25 microns to about 150 microns.

18. The method of claim 13, wherein said solid support is a membrane.

19. The method of claim 13, wherein said solid support is a monolith.

20. The method of claim 13, wherein said source solution contains a salt selected from alkali and alkaline earth metal halides at a concentration of about 50 mM to about 300 mM.

21. A method for purifying a protein from a source solution, said method comprising:
   i) contacting said source solution at a pH of 4.0 to 6.0 with the mixed-mode chromatography medium of claim 1; and
   ii) eluting said protein so bound from said solid support.

* * * * *